(12) United States Patent
Hayter et al.

(10) Patent No.: US 7,618,369 B2
(45) Date of Patent: Nov. 17, 2009

(54) METHOD AND SYSTEM FOR DYNAMICALLY UPDATING CALIBRATION PARAMETERS FOR AN ANALYTE SENSOR

(75) Inventors: Gary Hayter, Oakland, CA (US); Erwin S. Budiman, Fremont, CA (US); Kenneth J. Doniger, Menlo Park, CA (US); John C. Mazza, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 457 days.

(21) Appl. No.: 11/537,991

(22) Filed: Oct. 2, 2006

(65) Prior Publication Data

US 2008/0081977 A1  Apr. 3, 2008

(51) Int. Cl.
*A61B 5/00* (2006.01)
(52) U.S. Cl. .................. 600/309; 600/345; 600/347; 600/365
(58) Field of Classification Search .................. 600/365, 600/300, 485–499, 309–361
See application file for complete search history.

(56) References Cited

U.S. PATENT DOCUMENTS

| | | | |
|---|---|---|---|
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,425,920 A | 1/1984 | Bourland et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,619,793 A | 10/1986 | Lee | |
| 4,671,288 A | 6/1987 | Gough | |
| 4,703,756 A | 11/1987 | Gough et al. | |
| 4,731,726 A | 3/1988 | Allen, III | |

(Continued)

FOREIGN PATENT DOCUMENTS

DE   4401400   7/1995

(Continued)

OTHER PUBLICATIONS

International Search Report and Written Opinion of the International Searching Authority for PCT Application No. PCT/US2007/079860 filed Sep. 28, 2007 to Abbott Diabetes Care, Inc.

(Continued)

*Primary Examiner*—Patricia C Mallari
*Assistant Examiner*—Jordan Golomb
(74) *Attorney, Agent, or Firm*—Jackson & Co., LLP

(57) ABSTRACT

Methods and apparatuses including determining a calibration parameter associated with a detected analyte value, calibrating the analyte value based on the calibration parameter, and dynamically updating the calibration parameter are disclosed. Also provided are systems, kits, and computer program products.

24 Claims, 8 Drawing Sheets

U.S. PATENT DOCUMENTS

| | | | |
|---|---|---|---|
| 4,749,985 A | 6/1988 | Corsberg | |
| 4,757,022 A | 7/1988 | Shults et al. | |
| 4,777,953 A | 10/1988 | Ash et al. | |
| 4,779,618 A | 10/1988 | Mund et al. | |
| 4,854,322 A | 8/1989 | Ash et al. | |
| 4,890,620 A | 1/1990 | Gough | |
| 4,925,268 A | 5/1990 | Iyer et al. | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,055,171 A | 10/1991 | Peck | |
| 5,068,536 A * | 11/1991 | Rosenthal | 250/341.5 |
| 5,082,550 A | 1/1992 | Rishpon et al. | |
| 5,106,365 A | 4/1992 | Hernandez | |
| 5,122,925 A | 6/1992 | Inpyn | |
| 5,165,407 A | 11/1992 | Wilson et al. | |
| 5,246,867 A | 9/1993 | Lakowicz et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,390,671 A | 2/1995 | Lord et al. | |
| 5,391,250 A | 2/1995 | Cheney, II et al. | |
| 5,408,999 A | 4/1995 | Singh et al. | |
| 5,411,647 A | 5/1995 | Johnson et al. | |
| 5,431,160 A | 7/1995 | Wilkins | |
| 5,431,921 A | 7/1995 | Thombre | |
| 5,462,645 A | 10/1995 | Albery et al. | |
| 5,497,772 A * | 3/1996 | Schulman et al. | 600/347 |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,586,553 A | 12/1996 | Halili et al. | |
| 5,593,852 A | 1/1997 | Heller et al. | |
| 5,609,575 A | 3/1997 | Larson et al. | |
| 5,628,310 A | 5/1997 | Rao et al. | |
| 5,653,239 A | 8/1997 | Pompei et al. | |
| 5,665,222 A | 9/1997 | Heller et al. | |
| 5,711,001 A | 1/1998 | Bussan et al. | |
| 5,711,861 A | 1/1998 | Ward et al. | |
| 5,772,586 A | 6/1998 | Heinonen et al. | |
| 5,791,344 A | 8/1998 | Schulman et al. | |
| 5,899,855 A | 5/1999 | Brown | |
| 5,925,021 A | 7/1999 | Castellano et al. | |
| 5,942,979 A | 8/1999 | Luppino | |
| 5,957,854 A | 9/1999 | Besson et al. | |
| 5,964,993 A | 10/1999 | Blubaugh, Jr. et al. | |
| 5,965,380 A | 10/1999 | Heller et al. | |
| 5,971,922 A | 10/1999 | Arita et al. | |
| 5,995,860 A | 11/1999 | Sun et al. | |
| 6,001,067 A | 12/1999 | Shults et al. | |
| 6,024,699 A | 2/2000 | Surwit et al. | |
| 6,049,727 A | 4/2000 | Crothall | |
| 6,083,710 A | 7/2000 | Heller et al. | |
| 6,088,608 A | 7/2000 | Schulman et al. | |
| 6,091,976 A | 7/2000 | Pfeiffer et al. | |
| 6,093,172 A | 7/2000 | Funderburk et al. | |
| 6,103,033 A | 8/2000 | Say et al. | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,134,461 A | 10/2000 | Say et al. | |
| 6,162,611 A | 12/2000 | Heller et al. | |
| 6,175,752 B1 | 1/2001 | Say et al. | |
| 6,200,265 B1 | 3/2001 | Walsh et al. | |
| 6,212,416 B1 | 4/2001 | Ward et al. | |
| 6,219,574 B1 | 4/2001 | Cormier et al. | |
| 6,248,067 B1 | 6/2001 | Causey, III et al. | |
| 6,275,717 B1 | 8/2001 | Gross et al. | |
| 6,284,478 B1 | 9/2001 | Heller et al. | |
| 6,293,925 B1 | 9/2001 | Safabash et al. | |
| 6,295,506 B1 | 9/2001 | Heinonen et al. | |
| 6,306,104 B1 | 10/2001 | Cunningham et al. | |
| 6,309,884 B1 | 10/2001 | Cooper et al. | |
| 6,329,161 B1 | 12/2001 | Heller et al. | |
| 6,360,888 B1 | 3/2002 | McIvor et al. | |
| 6,366,794 B1 | 4/2002 | Moussy et al. | |
| 6,377,828 B1 | 4/2002 | Chaiken et al. | |
| 6,379,301 B1 | 4/2002 | Worthington et al. | |
| 6,424,847 B1 | 7/2002 | Mastrototaro et al. | |
| 6,427,088 B1 | 7/2002 | Bowman, IV et al. | |
| 6,440,068 B1 | 8/2002 | Brown et al. | |
| 6,478,736 B1 | 11/2002 | Mault | |
| 6,484,046 B1 | 11/2002 | Say et al. | |
| 6,514,718 B2 | 2/2003 | Heller et al. | |
| 6,551,494 B1 | 4/2003 | Heller et al. | |
| 6,558,321 B1 | 5/2003 | Burd et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,564,105 B2 | 5/2003 | Starkweather et al. | |
| 6,565,509 B1 | 5/2003 | Say et al. | |
| 6,571,128 B2 | 5/2003 | Lebel et al. | |
| 6,576,101 B1 | 6/2003 | Heller et al. | |
| 6,577,899 B2 | 6/2003 | Lebel et al. | |
| 6,579,690 B1 | 6/2003 | Bonnecaze et al. | |
| 6,585,644 B2 | 7/2003 | Lebel et al. | |
| 6,591,125 B1 | 7/2003 | Buse et al. | |
| 6,595,919 B2 | 7/2003 | Berner et al. | |
| 6,605,200 B1 | 8/2003 | Mao et al. | |
| 6,605,201 B1 | 8/2003 | Mao et al. | |
| 6,607,509 B2 | 8/2003 | Bobroff et al. | |
| 6,610,012 B2 | 8/2003 | Mault | |
| 6,633,772 B2 | 10/2003 | Ford et al. | |
| 6,635,014 B2 | 10/2003 | Starkweather et al. | |
| 6,648,821 B2 | 11/2003 | Lebel et al. | |
| 6,654,625 B1 | 11/2003 | Say et al. | |
| 6,659,948 B2 | 12/2003 | Lebel et al. | |
| 6,668,196 B1 | 12/2003 | Villegas et al. | |
| 6,687,546 B2 | 2/2004 | Lebel et al. | |
| 6,689,056 B1 | 2/2004 | Kilcoyne et al. | |
| 6,694,191 B2 | 2/2004 | Starkweather et al. | |
| 6,695,860 B1 | 2/2004 | Ward et al. | |
| 6,702,857 B2 | 3/2004 | Brauker et al. | |
| 6,733,446 B2 | 5/2004 | Lebel et al. | |
| 6,740,075 B2 | 5/2004 | Lebel et al. | |
| 6,741,877 B1 | 5/2004 | Shults et al. | |
| 6,746,582 B2 | 6/2004 | Heller et al. | |
| 6,758,810 B2 | 7/2004 | Lebel et al. | |
| 6,770,030 B1 | 8/2004 | Schaupp et al. | |
| 6,790,178 B1 | 9/2004 | Mault et al. | |

| | | | |
|---|---|---|---|
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,862,465 B2 | 3/2005 | Shults et al. | |
| 6,873,268 B2 | 3/2005 | Lebel et al. | |
| 6,881,551 B2 | 4/2005 | Heller et al. | |
| 6,892,085 B2 | 5/2005 | McIvor et al. | |
| 6,895,263 B2 * | 5/2005 | Shin et al. | 600/316 |
| 6,895,265 B2 | 5/2005 | Silver | |
| 6,931,327 B2 | 8/2005 | Goode, Jr. et al. | |
| 6,932,894 B2 | 8/2005 | Mao et al. | |
| 6,936,006 B2 | 8/2005 | Sabra | |
| 6,950,708 B2 | 9/2005 | Bowman, IV et al. | |
| 6,958,705 B2 | 10/2005 | Lebel et al. | |
| 6,968,294 B2 | 11/2005 | Gutta et al. | |
| 6,971,274 B2 | 12/2005 | Olin | |
| 6,974,437 B2 | 12/2005 | Lebel et al. | |
| 6,990,366 B2 | 1/2006 | Say et al. | |
| 6,997,907 B2 | 2/2006 | Safabash et al. | |
| 6,998,247 B2 | 2/2006 | Monfre et al. | |
| 7,003,336 B2 | 2/2006 | Holker et al. | |
| 7,003,340 B2 | 2/2006 | Say et al. | |
| 7,003,341 B2 | 2/2006 | Say et al. | |
| 7,024,245 B2 | 4/2006 | Lebel et al. | |
| 7,029,444 B2 * | 4/2006 | Shin et al. | 600/365 |
| 7,041,068 B2 | 5/2006 | Freeman et al. | |
| 7,052,483 B2 | 5/2006 | Wojcik | |
| 7,056,302 B2 | 6/2006 | Douglas | |
| 7,074,307 B2 | 7/2006 | Simpson et al. | |
| 7,081,195 B2 | 7/2006 | Simpson et al. | |
| 7,098,803 B2 | 8/2006 | Mann et al. | |
| 7,108,778 B2 | 9/2006 | Simpson et al. | |
| 7,110,803 B2 | 9/2006 | Shults et al. | |
| 7,113,821 B1 | 9/2006 | Sun et al. | |
| 7,134,999 B2 | 11/2006 | Brauker et al. | |
| 7,136,689 B2 | 11/2006 | Shults et al. | |
| 7,171,274 B2 | 1/2007 | Starkweather et al. | |
| 7,190,988 B2 | 3/2007 | Say et al. | |
| 7,192,450 B2 | 3/2007 | Brauker et al. | |
| 7,198,606 B2 | 4/2007 | Boecker et al. | |
| 7,226,978 B2 | 6/2007 | Tapsak et al. | |
| 7,276,029 B2 * | 10/2007 | Goode et al. | 600/365 |
| 7,299,082 B2 * | 11/2007 | Feldman et al. | 600/347 |
| 7,310,544 B2 | 12/2007 | Brister et al. | |
| 7,335,294 B2 | 2/2008 | Heller et al. | |
| 2002/0019022 A1 | 2/2002 | Dunn et al. | |
| 2002/0042090 A1 | 4/2002 | Heller et al. | |
| 2002/0103499 A1 | 8/2002 | Perez et al. | |
| 2002/0106709 A1 | 8/2002 | Potts et al. | |
| 2002/0128594 A1 | 9/2002 | Das et al. | |
| 2002/0161288 A1 * | 10/2002 | Shin et al. | 600/316 |
| 2003/0023317 A1 | 1/2003 | Brauker et al. | |
| 2003/0032874 A1 | 2/2003 | Rhodes et al. | |
| 2003/0042137 A1 | 3/2003 | Mao et al. | |
| 2003/0065308 A1 | 4/2003 | Lebel et al. | |
| 2003/0134347 A1 | 7/2003 | Heller et al. | |
| 2003/0168338 A1 | 9/2003 | Gao et al. | |
| 2003/0176933 A1 | 9/2003 | Lebel et al. | |
| 2003/0187338 A1 | 10/2003 | Say et al. | |
| 2003/0199790 A1 | 10/2003 | Boecker et al. | |
| 2003/0212379 A1 | 11/2003 | Bylund et al. | |
| 2003/0217966 A1 | 11/2003 | Tapsak et al. | |
| 2004/0010207 A1 | 1/2004 | Flaherty et al. | |
| 2004/0011671 A1 | 1/2004 | Shults et al. | |
| 2004/0040840 A1 | 3/2004 | Mao et al. | |
| 2004/0045879 A1 | 3/2004 | Shults et al. | |
| 2004/0064068 A1 | 4/2004 | DeNuzzio et al. | |
| 2004/0106858 A1 | 6/2004 | Say et al. | |
| 2004/0122353 A1 | 6/2004 | Shahmirian et al. | |
| 2004/0133164 A1 | 7/2004 | Funderburk et al. | |
| 2004/0138588 A1 | 7/2004 | Saikley et al. | |
| 2004/0152622 A1 | 8/2004 | Keith et al. | |
| 2004/0167801 A1 | 8/2004 | Say et al. | |
| 2004/0171921 A1 | 9/2004 | Say et al. | |
| 2004/0176672 A1 | 9/2004 | Silver et al. | |
| 2004/0186362 A1 | 9/2004 | Brauker et al. | |
| 2004/0186365 A1 | 9/2004 | Jin et al. | |
| 2004/0193090 A1 | 9/2004 | Lebel et al. | |
| 2004/0199059 A1 | 10/2004 | Brauker et al. | |
| 2004/0204687 A1 | 10/2004 | Mogensen et al. | |
| 2004/0225338 A1 | 11/2004 | Lebel et al. | |
| 2004/0236200 A1 | 11/2004 | Say et al. | |
| 2004/0254433 A1 | 12/2004 | Bandis et al. | |
| 2004/0267300 A1 | 12/2004 | Mace | |
| 2005/0004494 A1 | 1/2005 | Perez et al. | |
| 2005/0010269 A1 | 1/2005 | Lebel et al. | |
| 2005/0027177 A1 | 2/2005 | Shin et al. | |
| 2005/0031689 A1 | 2/2005 | Shults et al. | |
| 2005/0043598 A1 | 2/2005 | Goode, Jr. et al. | |
| 2005/0090607 A1 | 4/2005 | Tapsak et al. | |
| 2005/0112169 A1 | 5/2005 | Brauker et al. | |
| 2005/0114068 A1 | 5/2005 | Chey et al. | |
| 2005/0121322 A1 | 6/2005 | Say et al. | |
| 2005/0131346 A1 | 6/2005 | Douglas | |
| 2005/0143635 A1 | 6/2005 | Kamath et al. | |
| 2005/0176136 A1 | 8/2005 | Burd et al. | |
| 2005/0182306 A1 | 8/2005 | Sloan | |
| 2005/0187720 A1 | 8/2005 | Goode, Jr. et al. | |
| 2005/0192557 A1 | 9/2005 | Brauker et al. | |
| 2005/0195930 A1 | 9/2005 | Spital et al. | |
| 2005/0199494 A1 | 9/2005 | Say et al. | |
| 2005/0203360 A1 * | 9/2005 | Brauker et al. | 600/345 |
| 2005/0239154 A1 | 10/2005 | Feldman et al. | |
| 2005/0241957 A1 | 11/2005 | Mao et al. | |
| 2005/0245795 A1 | 11/2005 | Goode, Jr. et al. | |
| 2005/0245799 A1 | 11/2005 | Brauker et al. | |
| 2005/0287620 A1 | 12/2005 | Heller et al. | |
| 2006/0001538 A1 | 1/2006 | Kraft et al. | |
| 2006/0015020 A1 | 1/2006 | Neale et al. | |
| 2006/0015024 A1 | 1/2006 | Brister et al. | |
| 2006/0016700 A1 | 1/2006 | Brister et al. | |
| 2006/0019327 A1 | 1/2006 | Brister et al. | |
| 2006/0020186 A1 | 1/2006 | Brister et al. | |
| 2006/0020187 A1 | 1/2006 | Brister et al. | |
| 2006/0020188 A1 * | 1/2006 | Kamath et al. | 600/345 |
| 2006/0020189 A1 | 1/2006 | Brister et al. | |
| 2006/0020190 A1 | 1/2006 | Kamath et al. | |
| 2006/0020191 A1 | 1/2006 | Brister et al. | |
| 2006/0020192 A1 | 1/2006 | Brister et al. | |
| 2006/0036139 A1 | 2/2006 | Brister et al. | |
| 2006/0036140 A1 | 2/2006 | Brister et al. | |
| 2006/0036141 A1 | 2/2006 | Kamath et al. | |
| 2006/0036142 A1 | 2/2006 | Brister et al. | |
| 2006/0036143 A1 | 2/2006 | Brister et al. | |
| 2006/0036144 A1 | 2/2006 | Brister et al. | |
| 2006/0036145 A1 | 2/2006 | Brister et al. | |
| 2006/0166629 A1 | 7/2006 | Reggiardo | |
| 2006/0173444 A1 | 8/2006 | Choy et al. | |
| 2006/0183985 A1 | 8/2006 | Brister et al. | |
| 2006/0189863 A1 | 8/2006 | Heller et al. | |
| 2006/0222566 A1 | 10/2006 | Brauker et al. | |
| 2006/0229512 A1 | 10/2006 | Petisce et al. | |
| 2006/0247508 A1 | 11/2006 | Fennell | |
| 2007/0027381 A1 | 2/2007 | Stafford | |
| 2007/0060814 A1 | 3/2007 | Stafford | |
| 2007/0073129 A1 | 3/2007 | Shah et al. | |
| 2007/0078320 A1 | 4/2007 | Stafford | |
| 2007/0078321 A1 | 4/2007 | Mazza et al. | |
| 2007/0078322 A1 | 4/2007 | Stafford | |
| 2007/0106135 A1 | 5/2007 | Sloan et al. | |
| 2007/0149875 A1 | 6/2007 | Ouyang et al. | |
| 2007/0163880 A1 | 7/2007 | Woo et al. | |
| 2007/0173706 A1 | 7/2007 | Neinast et al. | |
| 2007/0191701 A1 | 8/2007 | Feldman et al. | |

| | | | |
|---|---|---|---|
| 2007/0203407 | A1 | 8/2007 | Hoss et al. |
| 2007/0203966 | A1 | 8/2007 | Brauker et al. |
| 2007/0235331 | A1 | 10/2007 | Simpson et al. |
| 2007/0249922 | A1 | 10/2007 | Peyser et al. |
| 2008/0009692 | A1 | 1/2008 | Stafford |
| 2008/0017522 | A1 | 1/2008 | Heller et al. |
| 2008/0021666 | A1 | 1/2008 | Goode, Jr. et al. |
| 2008/0029391 | A1 | 2/2008 | Mao et al. |
| 2008/0039702 | A1 | 2/2008 | Hayter et al. |
| 2009/0062635 | A1* | 3/2009 | Brauker et al. ............ 600/365 |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/58537 | 8/2002 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/089103 | 9/2005 |
| WO | WO-2006/024671 | 3/2006 |
| WO | WO-2006/079114 | 7/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |

OTHER PUBLICATIONS

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceeding sof SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain The Newest Short-Range Connectivity Technology", *Smart Computing Learning Series, Wireless Computing* vol. 8, Issue 5 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 16 Pages.

McGarraugh, G., et al., "Physiological Influences on Off-Finger Glucose Testing", *Diabetes Technology & Therapeutics*, vol. 3 No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, Vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

International Preliminary Report on Patentability and Written Opinion of the International Searching Authority for PCT Application No. PCT/US2007/079860 filed Sep. 28, 2007, mailed Apr. 16, 2009.

* cited by examiner

METHOD AND SYSTEM FOR DYNAMICALLY UPDATING CALIBRATION PARAMETERS FOR AN ANALYTE SENSOR

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another portion of segment of the analyte sensor that is in communication with the transmitter unit. The transmitter unit is configured to transmit the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels.

To obtain accurate data from the analyte sensor, calibration is necessary. Typically, blood glucose measurements are periodically obtained using, for example, a blood glucose meter, and the measured blood glucose values are used to calibrate the sensors. Indeed, the patient must calibrate each new analyte sensor using for example, capillary blood glucose measurements. Due to a lag factor between the monitored data and the measured blood glucose values, an error is typically introduced in the monitored data.

In view of the foregoing, it would be desirable to have a method and system for calibrating analyte sensors of an analyte monitoring system to minimize the lag error and compensation of such lag errors in analyte monitoring systems.

SUMMARY OF THE INVENTION

In one embodiment, a method including determining a calibration parameter associated with a detected analyte value, calibrating the analyte value based on the calibration parameter, and dynamically updating the calibration parameter is disclosed.

These and other objects, features and advantages of the present invention will become more fully apparent from the following detailed description of the embodiments, the appended claims and the accompanying drawings.

DETAILED DESCRIPTION

As described in further detail below, in accordance with the various embodiments of the present invention, there is provided a method and system for calibration of analyte sensors to reduce errors in the sensor measurements. In particular, within the scope of the present invention, there are provided method and system for calibrating subcutaneous or transcutaneously positioned analyte sensors to compensate for lag errors associated with the estimated sensor sensitivity.

Figure 1:
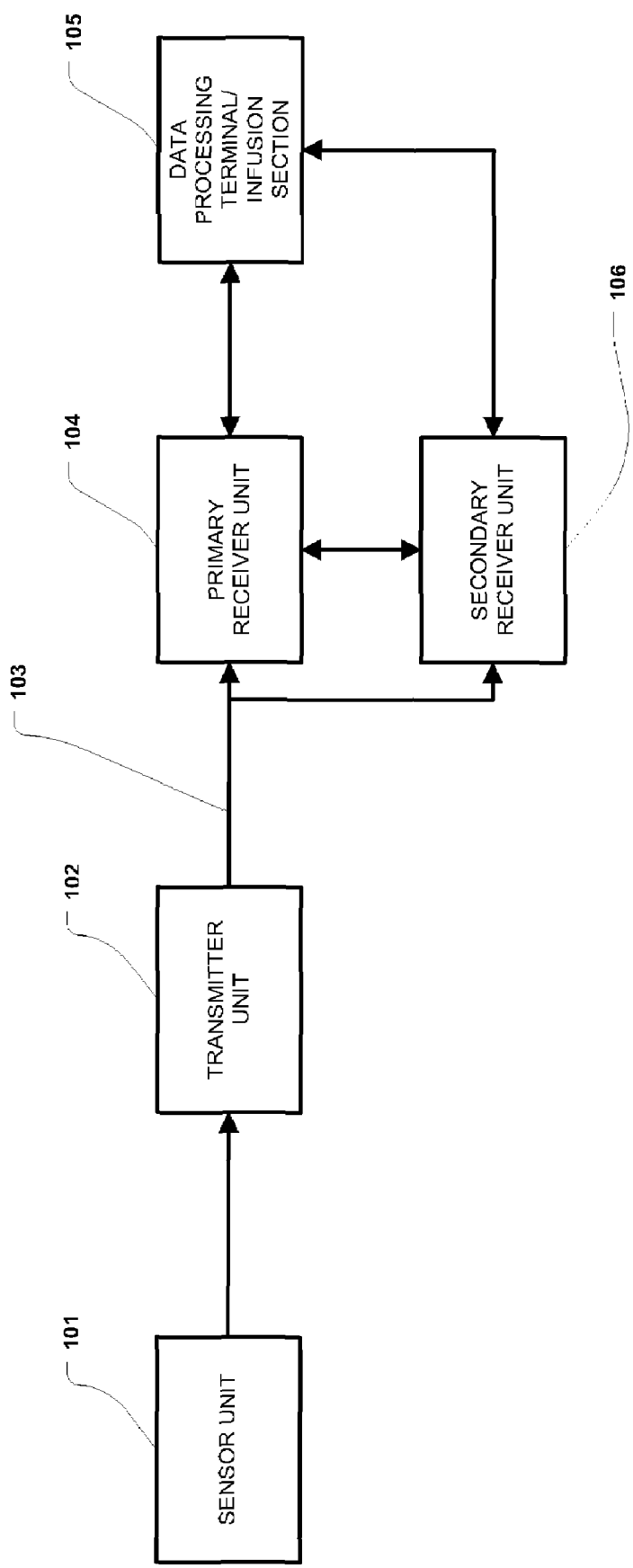
FIG. 1 illustrates a block diagram of a data monitoring and management system for practicing one or more embodiments of the present invention.

FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal in one embodiment may be configured to receive data directly from the transmitter unit 102 via a communication link 106 which may optionally be configured for bi-directional communication.

Also shown in FIG. 1 is a secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present invention, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 106, where the communication link 106, as described above, may be configured for bi-directional communication.

In this embodiment, the data processing terminal 105 which may include an insulin pump, may be configured to receive the analyte signals from the transmitter unit 102, and thus, incorporate the functions of the receiver 103 including data processing for managing the patient's insulin therapy and analyte monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Figure 2:
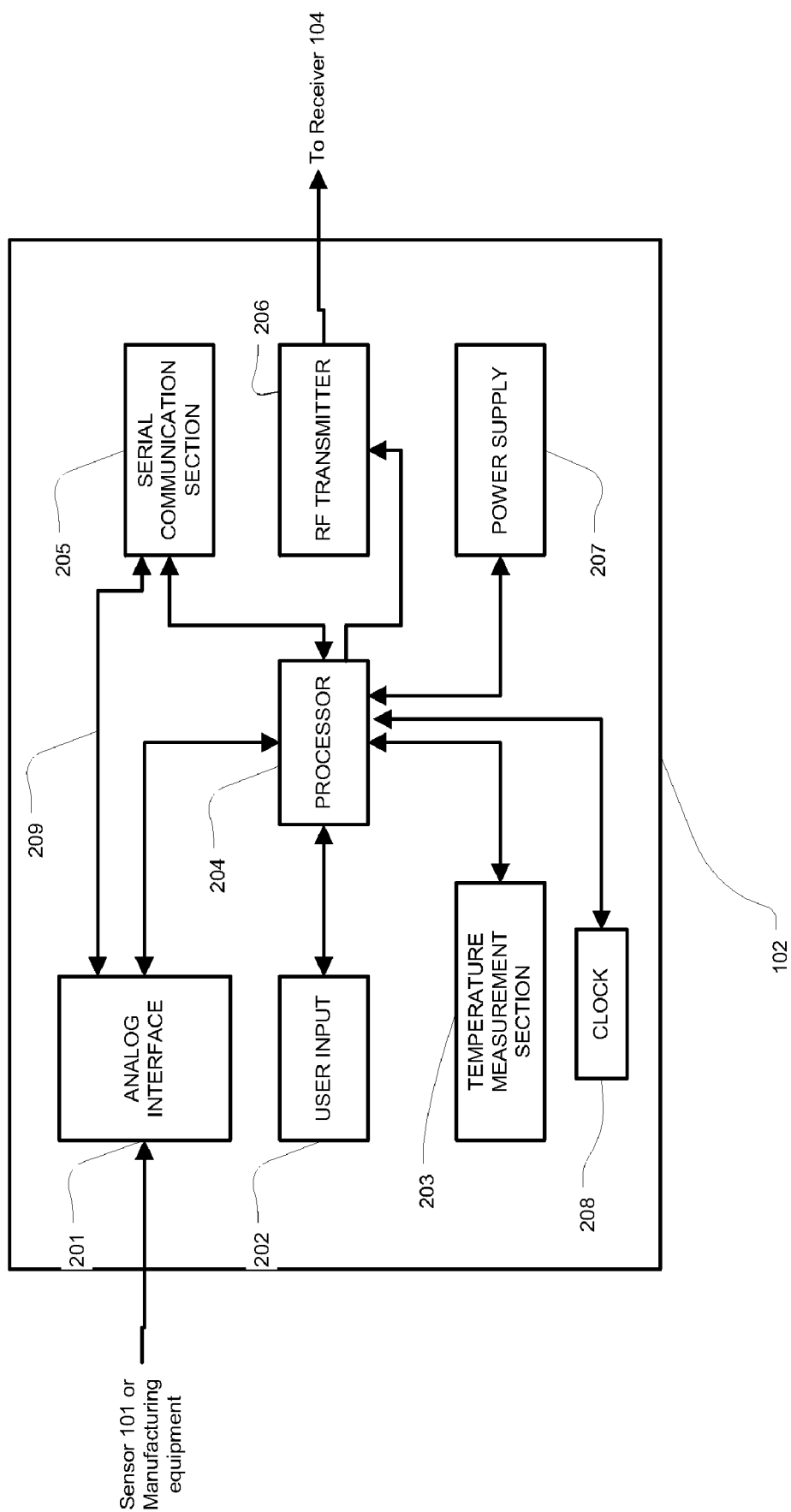
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter unit 102 for connection to the sensor unit 201 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard electrode (G) 211 and the processor 204 in the transmitter unit 102 of the data monitoring and management system 100. The leak detection circuit 214 in accordance with one embodiment of the present invention may be configured to detect leakage current in the sensor 101 to determine whether the measured sensor data are corrupt or whether the measured data from the sensor 101 is accurate.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application.

Figure 3:
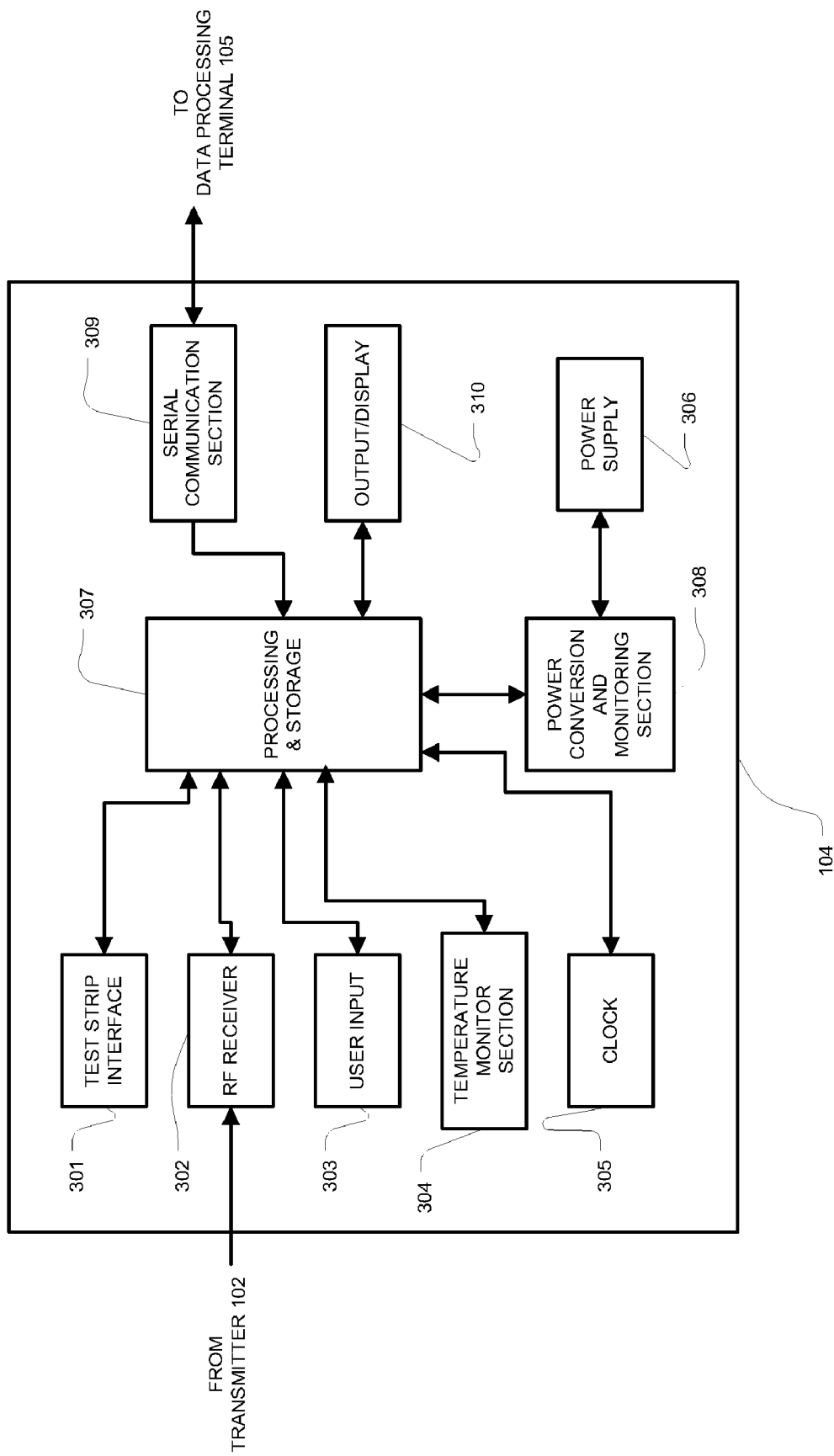
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the primary receiver unit 104 includes a blood glucose test strip interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307.

Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 104 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 is further configured to perform Manchester decoding as well as error detection and correction upon the encoded data signals received from the transmitter unit 102 via the communication link 103.

Figure 4:
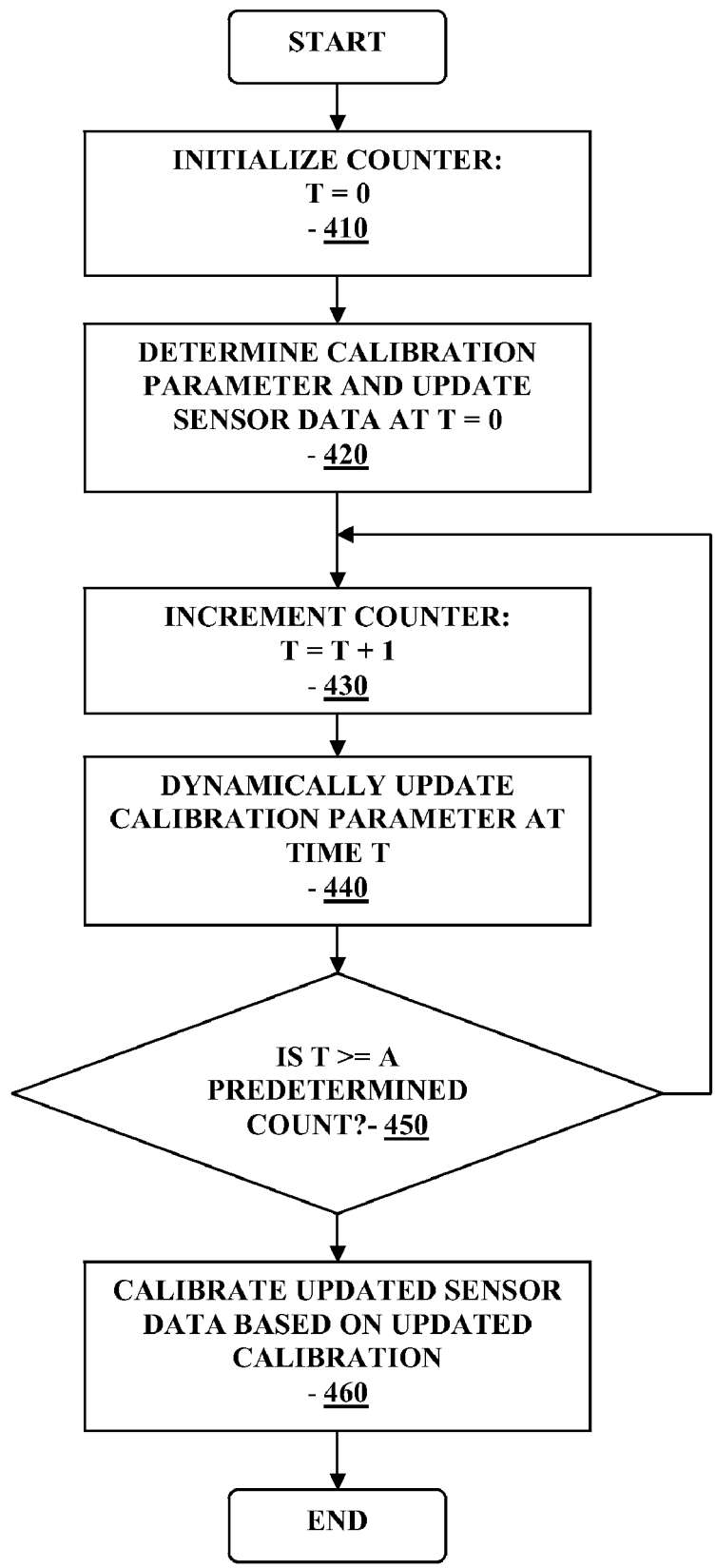
FIG. 4 is a flowchart illustrating an overall dynamically updating calibration in accordance with one embodiment of the present invention.

FIG. 4 is a flowchart illustrating an overall dynamically updating calibration in accordance with one embodiment of the present invention. Referring to FIG. 4, a counter such as a calibration counter is triggered to perform calibration of the monitored data such as the analyte data received from the transmitter unit 102 (FIG. 1). In one embodiment, the calibration counter may include a timer or a clock which may be configured to prompt the user or the patient to initiate the acquisition of reference data at a predetermined time intervals. When the calibration counter is initially triggered, the time counter T is initialized to zero (0). Thereafter, a calibration parameter is determined based on, for example, the acquired reference data and the monitored sensor data at time T=0. Moreover, in one embodiment, the monitored sensor data may be updated based on the calibration parameter. In one embodiment, the calibration parameter may include a sensor sensitivity value associated with the analyte sensor 101 (FIG. 1) configured to monitor the analyte levels of the patient.

As described in further detail below, for example, in conjunction with FIG. 5, in particular embodiments, during the initial calibration stage at T=0, a reference glucose value is determined, for example, such as a capillary blood glucose value using a blood glucose meter such as FREESTYLE® meter or PRECISION XTRA™ meter available from Abbott Diabetes Care Inc., Alameda, Calif. In addition, the monitored sensor data at or near the calibration time (T=0) is retrieved which may include the monitored sensor data at time T=T−1, at time T=T+1, or any other suitable time period (for example, from the processing and storage unit 307 (FIG. 3) of the receiver unit 104 (FIG. 1).

More specifically, in one embodiment, the monitored sensor data at the calibration time (T=0) may include one or more monitored sensor data in addition to the monitored sensor data point at the calibration time (T=0). That is, in one embodiment, the monitored sensor data at the calibration time (T=0) may include all monitored sensor data available for retrieval from the receiver unit 104 (FIG. 1) at the calibration time (T=0). For example, to reduce the contribution of noise in the measured sensor data, an average of the two most recent sensor data may be associated with the monitored sensor data at the calibration time (T=0).

Broadly, within the scope of the present disclosure, the monitored sensor data at a predetermined time may include, in particular embodiments, an estimate of the sensor data at the predetermined time as determined by the one or more filters which may be configured to use the monitored sensor data up to and including the data point at the predetermined time (for example, up to the data point at calibration time (T=0)). In one embodiment, one or more filters such as a finite impulse response (FIR) filter may be used to determine the best estimate at a predetermined time using a finite window of monitored sensor data up to the current or most recent monitored sensor data point.

Referring back to FIG. 4, after determining the calibration parameter and updating the monitored data at the calibration time (T=0), the counter is incremented by one (1), and dynamic, real-time update of the calibration parameter is performed. In one embodiment, the counter may be configured to increment by one with each reception of sensor data from the transmitter unit 102 (FIG. 1). After dynamically updating the calibration parameter at the subsequent incremented time (T=1), it is determined whether the counter has reached a predetermined count (for example, set at seven (7)). If it is determined that the counter has not reached the predetermined count, then the routine in one embodiment returns to step 430 where the counter is incremented by one (1) and the dynamically updating calibration parameter and monitored sensor data is performed for monitored data at the second subsequent incremented time (T=2).

On the other hand, if it is determined that the counter has reached the predetermined count, then in one embodiment, subsequent monitored sensor data may be updated based on the dynamically updated calibration parameter and/or updated monitored sensor data. Thereafter, in particular embodiments, it is determined whether further or subsequent lag correction will likely not yield more accurate monitored data value (or with less errors). Therefore, in one embodiment, the routine terminates and awaits for the subsequent calibration time, for example, to repeat the processes described above in conjunction with FIG. 4.

In this manner, within the scope of the present disclosure, there are provided methods and system for dynamically, and in particular embodiments, in real-time, obtaining reference data at a first predetermined time, receiving measured data prior to and including (or near) the first predetermined time, calculating a first calibration parameter (or parameters) using the data, calibrating the measured data based on the calibration parameter, receiving measured data at a second predetermined time, updating the calibration parameter based on all of the previous data and the newly received measured data, calibrating the newly received measured data based on the updated calibration parameter, and repeating a number of time the process of receiving new measurement data, updating the calibration parameter, calibrating the newly received measurement data, and calibrating any newly received measurement data with the fully updated calibration parameter.

A method in a further embodiment may include performing lag compensation on the measured data that is used to update the calibration parameter. Lag compensation may optionally be performed on the measured data that is calibrated. A method in a further embodiment includes filtering the measured data that is used to update the calibration parameter.

Figure 5:
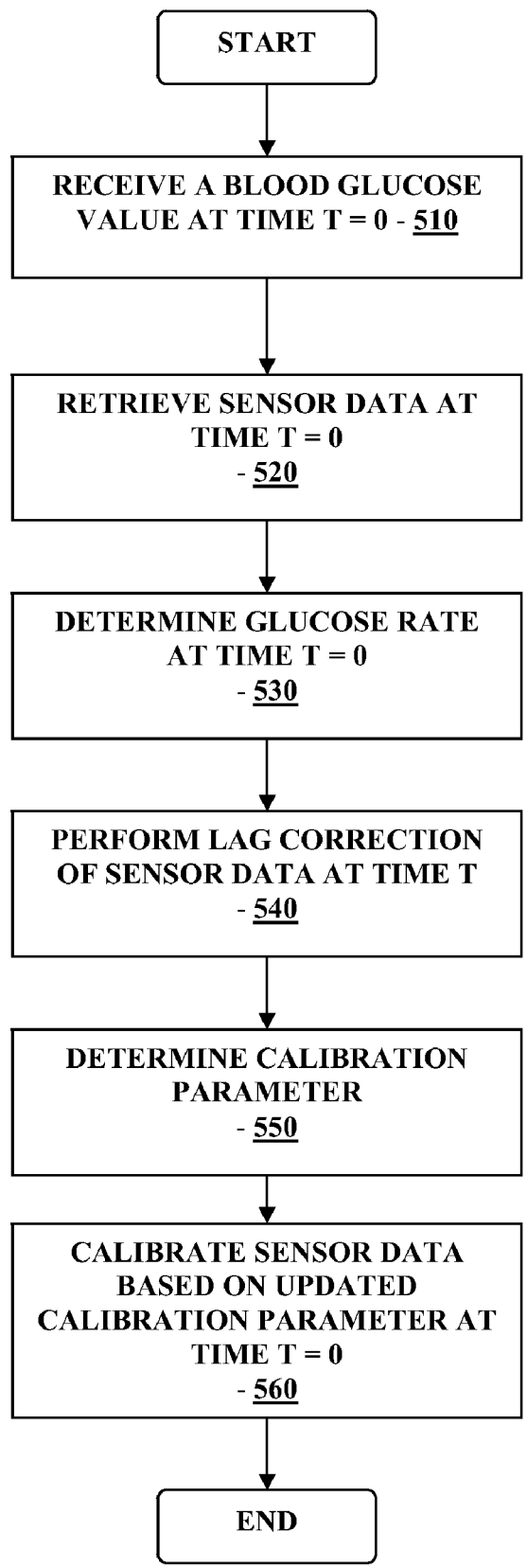
FIG. 5 is a flowchart illustrating the lag correction and calibration routine of the overall dynamically updating calibration shown in FIG. 4 in accordance with one embodiment of the present invention.

FIG. 5 is a flowchart illustrating the lag correction and calibration routine of the overall dynamically updating calibration shown in FIG. 4 in accordance with one embodiment of the present invention. Referring to FIG. 5, the determination of calibration parameter and updating the monitored analyte level at the calibration time (T=0) is described in further detail. More specifically, in one embodiment, a capillary blood glucose value is determined at the calibration time (T=0), and the monitored analyte value at the calibration time is retrieved from the receiver unit 104 of the monitoring system 100 (FIG. 1).

Thereafter, a rate of change of the monitored data at the calibration time (T=0) is determined. In one embodiment, the rate of change of the monitored data at the calibration time (T=0) may be determined using one or more filters including, but not limited to infinite impulse response (IIR) filter, finite impulse response (FIR) filter, backward and/or forward smoothing techniques (e.g., Kalman filtering technique), or any other equivalent one or more causal filters that balance signal noise reduction with lag correction.

Upon determining the rate of change of the monitored data at the calibration time (T=0), the monitored data at the calibration time (T=0) is updated. In one embodiment, the updated monitored sensor data may include lag corrected monitored data at the calibration time (T=0). Optionally, the lag correction for the monitored data at the calibration time (T=0) may be skipped and not performed. In one embodiment, the lag corrected monitored data at the calibration time (T=0) may be determined by applying the determined rate of change of the monitored data at the calibration time (T=0) to a predetermined constant value. In one embodiment, the predetermined constant value may include, a predetermined time constant.

For example, in one embodiment, the predetermined time constant may include a fixed time constant in the range of approximately four to fifteen minutes, and which may be associated with the one or more of the patient physiological profile, one or more attributes associated with the monitoring system 100 (including, for example but not limited to, the characteristics of the analyte sensor 101). In a further aspect, the predetermined time constant may vary based on one or more factors including, for example, but not limited to the timing and amount of food intake by the patient, exogenous insulin intake, physical activities by the patient such as exercise, or any other factors that may affect the time constant, and which may be empirically determined.

Referring again to FIG. 5, the calibration parameter (for example, the sensitivity of the analyte sensor 101 FIG. 1), may be determined for example, in one embodiment, by determining the ratio of the monitored data (optionally lag corrected) at the calibration time (T=0) and the reference data obtained using, for example, the blood glucose meter as described above. In one embodiment, the calibration parameter may be determined by dividing the monitored data at the calibration time (T=0) by the reference data such as the capillary blood glucose value at the calibration time (T=0).

Thereafter, in one embodiment, the calibrated and updated monitored sensor data at the calibration time (T=0) is determined based upon the monitored data (optionally lag corrected) and the calibration parameter as determined above. For example, in one embodiment, the calibrated and updated monitored sensor data at the calibration time (T=0) may be determined by dividing the lag corrected monitored data at calibration time (T=0) by the determined calibration parameter.

Figure 6:
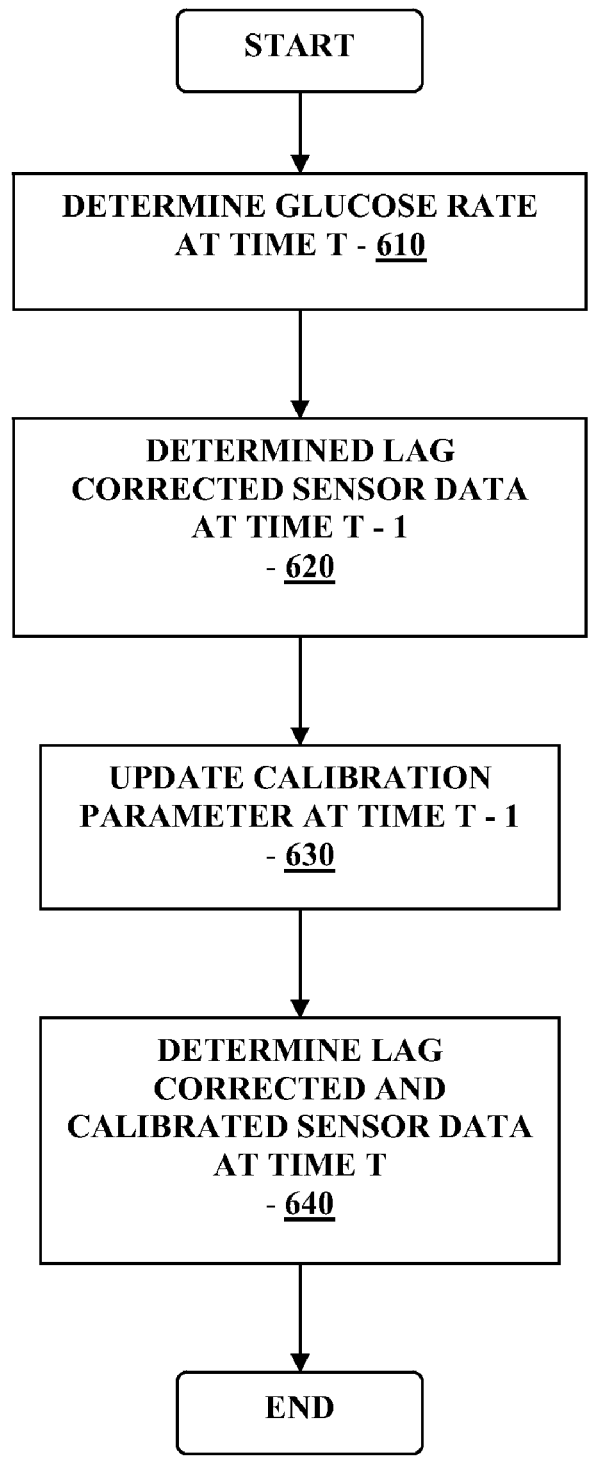
FIG. 6 is a flowchart illustrating the lag correction and dynamically updating calibration routine of the overall dynamically updating calibration shown in FIG. 4 in accordance with one embodiment of the present invention.

FIG. 6 is a flowchart illustrating the lag correction and dynamically updating calibration routine of the overall dynamically updating calibration shown in FIG. 4 in accordance with one embodiment of the present invention. Referring to FIGS. 4 and 6, with the counter incremented by one (see step 430 of FIG. 4), the analyte value at the subsequent incremented time (T=1) is retrieved from, for example, the processing and storage unit 307 (FIG. 3) of the receiver unit 104. In particular, in one embodiment, the rate of change of the monitored data at the calibration time (T=0) is updated based on the monitored data value at the subsequent incremented time (T=1). In other words, with the monitored data values at calibration time (T=0) and prior data and at the subsequent incremented time (T=1), the rate of change of the monitored data at the calibration time (T=0) may be estimated with an improved accuracy. Again, in one embodiment, the rate of change may be determined based on one or more not limited to infinite impulse response (IIR) filter, finite impulse response (FIR) filter, backward and/or forward smoothing techniques (e.g., Kalman filtering technique), or any other equivalent filtering or smoothing techniques.

With the updated rate of change at the calibration time (T=0) determined, monitored data (optionally lag corrected) at calibration time (T=0) is updated. That is, in one embodiment, the lag corrected sensor data at the calibration time (T=0) is updated based on the prior lag corrected and calibrated data at calibration time (T=0), and in conjunction with the predetermined constant (for example, the predetermined time constant discussed above), and the updated rate of change of the monitored data at the calibration time (T=0).

For example, in one embodiment, the lag corrected monitored data at the calibration time (T=0) is updated or determined by taking the sum of the lag corrected and calibration sensor value at calibration time (T=0) as determined above, with the updated rate of change of monitored data at calibration time (T=0) multiplied by the predetermined constant. In other words, in one embodiment, the updated rate of change of the monitored data at calibration time (T=0) may be multiplied by the predetermined constant, and thereafter, the resulting value is added to the lag corrected and calibrated monitored data at the calibration time (T=0) previously determined (see for example, step 420).

Referring again to FIG. 6, after determining the updated lag corrected monitored data at calibration time (T=0) based on monitored data at the subsequent incremented time (T=1) as described above, in one embodiment, the calibration parameter (for example, the sensitivity of the sensor 101 (FIG. 1) is updated based on the updated lag corrected monitored data at calibration time (T=0) described above. In particular, in one embodiment, the calibration parameter may be updated by determining the ratio of the updated lag corrected monitored data at calibration time (T=0) and the reference value (for example, the capillary blood glucose value) determined at calibration time (T=0).

After updating the calibration parameter as described above, in one embodiment, the lag corrected and calibrated monitored data at the subsequent incremented time (T=1) is determined based on the updated calibration parameter value. For example, in one embodiment, the monitored sensor data at the subsequent incremented time (T=1) in one embodiment may be divided by the updated sensitivity to determine the dynamically lag corrected and calibrated monitored sensor data at the subsequent incremented time (T=1).

In another embodiment, the dynamically lag corrected and calibrated monitored sensor data at the subsequent incremented time (T=1) may be determined based on the updated calibration parameter and the dynamically lag corrected monitored sensor data at the subsequent incremented time (T=1). In this case, the dynamically updated sensor data at the subsequent incremented time (T=1) in one embodiment may be determined by calculating the rate of change of the monitored data at the subsequent incremented time (T=1) using similar filtering techniques as described above, and applying the predetermined constant (for example, the predetermined time constant discussed above), the result of which is then added to the detected or monitored data at the subsequent incremented time (T=1). In other words, in one embodiment, the calculated rate of change of the monitored data at the subsequent incremented time (T=1) is multiplied by the predetermined time constant, and the resulting value is added to the monitored data value at the subsequent incremented time (T=1). This sum in one embodiment represents the dynamically updated monitored sensor data at the subsequent incremented time (T=1).

In this manner, in one embodiment, lag correction of analyte sensor data may be pseudo-retrospectively (or substantially in real time) updated using the monitored analyte data stream substantially continuously detected by the sensor 101 (FIG. 1) with the dynamic updating of the calibration parameter. Thus, in one aspect, lag error or error due to lag compensation may be overcome by, for example, updating the sensor sensitivity retrospectively with each value of the detected or monitored analyte levels. Accordingly, in one embodiment, calibration inaccuracies due to change (for example, rapid acceleration) of analyte levels after performing discrete calibration may be mitigated by updating the calibration routine taking into consideration the near immediate post calibration analyte sensor data to obtain a more reliable and accurate value associated with the rate of change of the monitored analyte levels. In one embodiment, the overall system accuracy of the monitored and detected analyte values may be improved.

Figure 7:
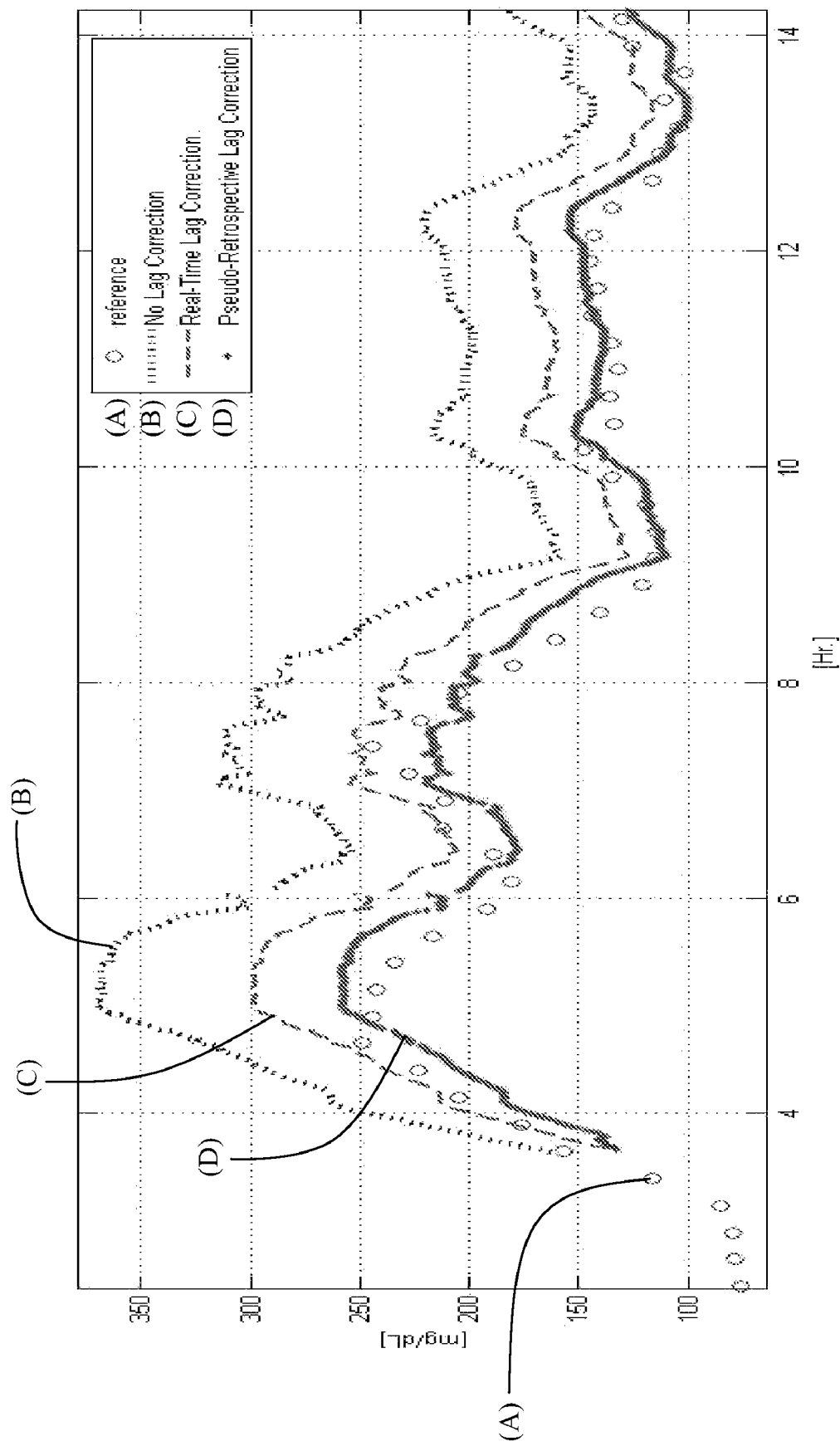
FIG. 7 illustrates an example of the lag corrected and calibrated sensor data in accordance with one embodiment of the present invention.

FIG. 7 illustrates an example of the lag corrected and calibrated sensor data in accordance with one embodiment of the present invention. Referring to FIG. 7, a comparison illustrating the improvement in calibration in the dynamically updated (for example, pseudo-retrospectively performed) lag correction approach in accordance with one embodiment is shown. Referring to FIG. 7, the reference data points (associated with the capillary blood glucose values) are shown as data points associated with legend (A), the no lag corrected monitored sensor data points are associated with legend (B), the lag corrected monitored sensor data points are associated with legend (C), and the dynamically updated monitored sensor data points are associated with legend (D).

Referring to FIG. 7, more specifically, when calibrating during a high rate of change (for example, between the $3^{rd}$ and $4^{th}$ hour in the Figure), and with uncorrected lag effects, an error in the sensitivity estimate is introduced. For the "No Lag Correction" trace (B), when the high rate of change subsides, it can be seen that the estimated glucose value is substantially overestimated compared to the reference values. When real time lag correction is introduced, it can be seen that the "Real Time Lag Correction" trace (C) is much closer to the reference values, but this is still a substantial overestimation, primarily when the glucose rate of change is negative (calibration occurred when the rate of change was positive). With the dynamic or pseudo-retrospective lag correction in accordance with one embodiment, it can be seen that the data values (shown with trace associated with legend (D)) match the reference values more accurately.

Figure 8:
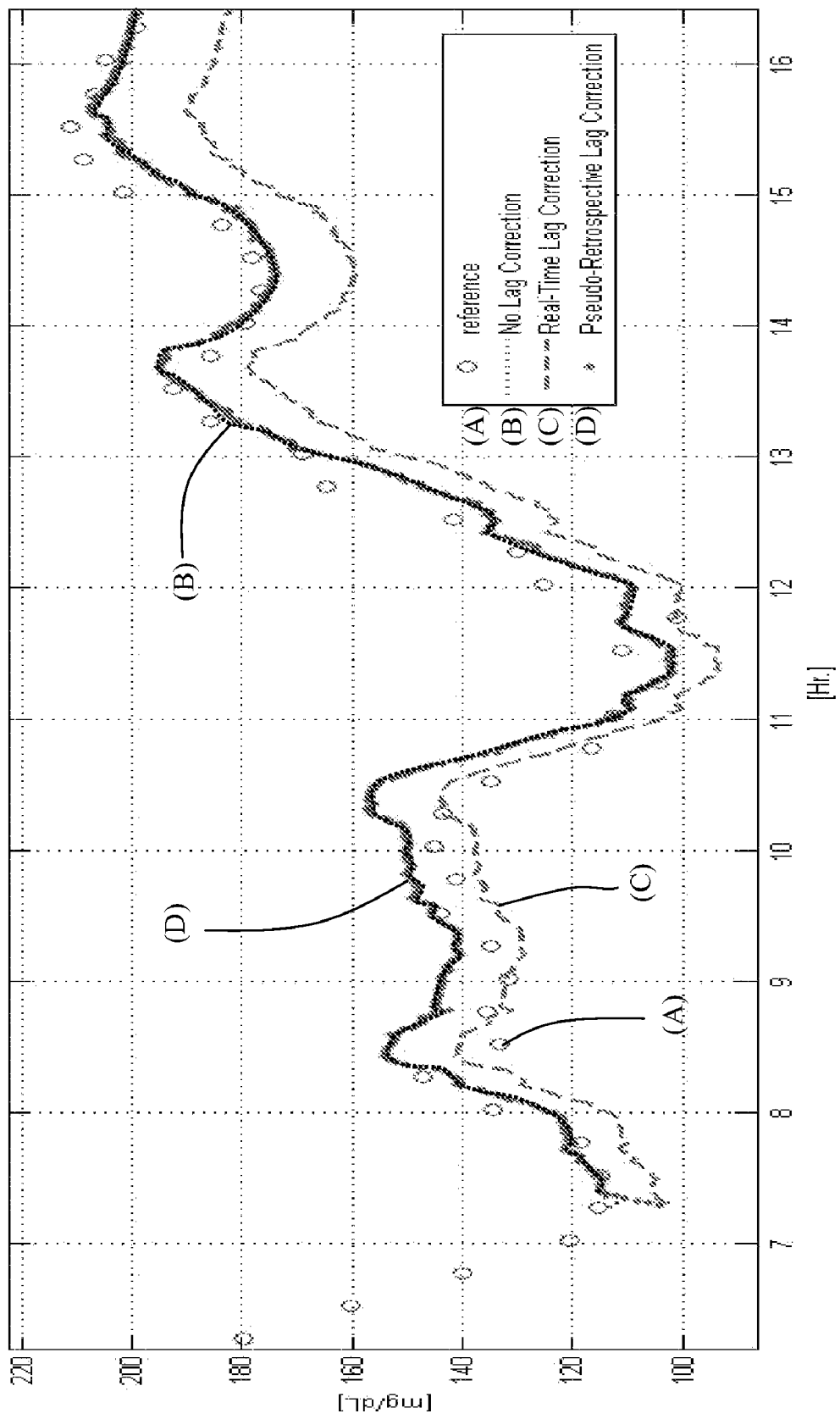
FIG. 8 illustrates a further example of the lag corrected and calibrated sensor data in accordance with one embodiment of the present invention.

FIG. 8 illustrates a further example of the lag corrected and calibrated sensor data in accordance with one embodiment of the present invention. Referring to FIG. 8, it can be seen that calibration occurs when the glucose rate-of-change is close to zero. Moreover, the real time lag correction signal is shown with a large error when the monitored glucose level is fluctuating, contrasted with the trace or curve associated with the pseudo-retrospective lag correction which, as can be seen from FIG. 8 substantially tracks the reference glucose values (e.g., measured from the capillary blood). Furthermore, it can be seen that in this example, the trace associated with no lag correction is substantially identical to the trace or curve associated with the pseudo-retrospective lag correction. This may result when the monitored analyte level is not changing during calibration, and thus there may be no lag error to correct, and which is factored in the approaches described in accordance with the various embodiments described herein.

Referring yet again to FIG. 8, it can be also seen that in certain cases, the real time lag correction may result in further distortion or more pronounced error factors as compared with the case where no lag correction is performed. Accordingly, in one embodiment, it can be seen from FIG. 8 that the pseudo-retrospective lag correction in accordance with the dynamically updating the calibration parameter and the monitored sensor data provides further accuracy and compensation of possible additional errors in the monitored sensor data. This can be seen by comparing the portions of the traces shown in FIG. 8 during the $11^{th}$ and the $12^{th}$ hours, where a rapid change in the monitored glucose values as a function of time adversely impacts the accuracy of the monitored data with real time lag correction (without the pseudo-retrospective lag correction including dynamically updated calibration parameter.

Referring to the Figures above, in particular embodiments, the pseudo-retrospective lag correction and calibration and updating of monitored sensor data may be performed by one or more processing units of the one or more receiver unit (104, 105) the transmitter unit 102 or the data processing terminal/infusion section 105. In addition, the one or more of the transmitter unit 102, the primary receiver unit 104, secondary receiver unit 105, or the data processing terminal/infusion section 105 may also incorporate a blood glucose meter functionality, such that, the housing of the respective one or more of the transmitter unit 102, the primary receiver unit 104, secondary receiver unit 105, or the data processing terminal/infusion section 105 may include a test strip port configured to receive a blood sample for determining one or more blood glucose levels of the patient.

In a further embodiment, the one or more of the transmitter unit 102, the primary receiver unit 104, secondary receiver unit 105, or the data processing terminal/infusion section 105 may be configured to receive the blood glucose value wirelessly over a communication link from, for example, a glucose meter. In still a further embodiment, the user or patient manipulating or using the analyte monitoring system 100 (FIG. 1) may manually input the blood glucose value using, for example, a user interface (for example, a keyboard, keypad, and the like) incorporated in the one or more of the transmitter unit 102, the primary receiver unit 104, secondary receiver unit 105, or the data processing terminal/infusion section 105.

A method in accordance with one embodiment of the present invention includes obtaining a reference data point at a first predetermined time, receiving a first data at the first predetermined time, calibrating the first data based on the reference data point, receiving a second data at a second predetermined time, updating the calibrated first data based on the second data, and calibrating the second data.

The reference data point may include a blood glucose value.

The first predetermined time may include a calibration time associated with the calibration of one or more of the first data or the second data.

The first data and the second data may include a respective one of a monitored analyte value.

In one embodiment, calibrating the first data may include determining a first rate of change of the first data at the first predetermined time, and performing a first lag compensation of the first data based on the first rate of change to generate a first lag compensated first data. In a further embodiment, calibrating the first data may include determining a first calibration parameter associated with the first data based on the reference data point and the first lag compensated first data, and generating a calibrated first data based on the first calibration parameter and the first lag compensated first data.

Updating the calibrated first data in one embodiment may include determining a second rate of change of the first data at the first predetermined time based on the second data, and performing a second lag compensation of the first data based on the second rate of change of the first data to generate a second lag compensated first data.

Also, calibrating the second data may include determining a second calibration parameter associated with the first data based on the reference data point and the second lag compensated first data, and generating a calibrated second data based on the second calibration parameter and the second lag compensated first data.

A method in accordance with another embodiment may include determining a calibration parameter associated with a detected analyte value, calibrating the analyte value based on the calibration parameter, and dynamically updating the calibration parameter.

The method in another aspect may include calibrating a second detected analyte value based on the dynamically updated calibration parameter.

Further, dynamically updating the calibration parameter may also include determining a rate of change of the detected analyte value, and generating a lag compensated analyte value based on the rate of change.

In addition, calibrating the analyte value may further include determining a sensitivity associated with the detected analyte value, and applying the sensitivity to the lag compensated analyte value.

Moreover, in still another embodiment, dynamically updating the calibration parameter may include updating the rate of change of the detected analyte value, and updating the lag compensated analyte value, where updating the rate of change may include determining the rate of change of the detected analyte value between a first predetermined time and a second predetermined time.

In still another embodiment, calibrating the analyte value may include detecting a calibration data, determining a sensitivity based on the calibration data and the lag compensated analyte value, and generating a lag compensated and calibrated analyte value.

An apparatus in accordance with another embodiment may include one or more processing units, and a memory for storing instructions which, when executed by the one or more processors, causes the one or more processing units to obtain a reference data point at a first predetermined time, receive a first data at the first predetermined time, calibrate the first data based on the reference data point; receive a second data at a second predetermined time; update the calibrated first data based on the second data; and calibrate the second data.

The memory in another aspect may be configured for storing instructions which, when executed by the one or more processing units, causes the one or more processing units to determine a first rate of change of the first data at the first predetermined time, and to perform a first lag compensation of the first data based on the first rate of change to generate a first lag compensated first data.

Moreover, the memory in yet another embodiment may be further configured for storing instructions which, when executed by the one or more processing units, causes the one or more processing units to determine a first calibration parameter associated with the first data based on the reference data point and the first lag compensated first data and to generate a calibrated first data based on the first calibration parameter and the first lag compensated first data.

Additionally, the memory may still be further configured for storing instructions which, when executed by the one or more processing units, causes the one or more processing units to determine a second rate of change of the first data at the first predetermined time based on the second data, and to perform a second lag compensation of the first data based on the second rate of change of the first data to generate a second lag compensated first data.

In yet still another aspect, the memory may be further configured for storing instructions which, when executed by the one or more processing units, causes the one or more processing units to determine a second calibration parameter associated with the first data based on the reference data point and the second lag compensated first data, and to generate a calibrated second data based on the second calibration parameter and the second lag compensated first data.

A method in accordance with still another embodiment of the present invention includes, dynamically, and in particular embodiments, in real-time, obtaining reference data at a first predetermined time, receiving measured data prior to and including (or near) the first predetermined time, calculating a first calibration parameter (or parameters) using the data, calibrating the measured data based on the calibration parameter, receiving measured data at a second predetermined time, updating the calibration parameter based on all of the previous data and the newly received measured data, calibrating the newly received measured data based on the updated calibration parameter, and repeating a number of time the process of receiving new measurement data, updating the calibration parameter, calibrating the newly received measurement data, and calibrating any newly received measurement data with the fully updated calibration parameter.

A method in a further embodiment includes performing lag compensation on the measured data that is used to update the calibration parameter. Lag compensation may optionally be performed on the measured data that is calibrated. A method in a further embodiment includes filtering the measured data that is used to update the calibration parameter.

An apparatus in accordance with yet still another embodiment includes one or more processing units, and a memory for storing instructions which, when executed by the one or more processors, causes the one or more processing units to dynamically, and in particular embodiments, in real-time, obtain reference data at a first predetermined time, retrieve measured data prior to and including (or near) the first predetermined time, calculate a first calibration parameter (or parameters) using the data, calibrate the measured data based on the calibration parameter, retrieve measured data at a second predetermined time, update the calibration parameter based on all of the previous data and the newly received measured data, calibrate the newly received measured data based on the updated calibration parameter, and repeat a number of time the process of receiving new measurement data, updating the calibration parameter, calibrating the newly received measurement data, and calibrating any newly received measurement data with the fully updated calibration parameter.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A computer implemented method, comprising:
   obtaining a reference data point at a first predetermined time determined based on an analyte sample from an in vitro test strip;
   receiving a first data at the first predetermined time from an analyte sensor in fluid contact with an interstitial fluid;
   calibrating the first data based on the reference data point using a processor;
   receiving a second data at a second predetermined time from the analyte sensor;
   updating the calibrated first data based on the second data; and
   calibrating the second data.

2. The method of claim 1 wherein the reference data point includes a blood glucose value.

3. The method of claim 1 wherein the first predetermined time includes a calibration time associated with the calibration of one or more of the first data or the second data.

4. The method of claim 1 wherein the first data and the second data includes a respective one of a monitored analyte value.

5. The method of claim 1 wherein calibrating the first data includes:
   determining a first rate of change of the first data at the first predetermined time; and
   performing a first lag compensation of the first data based on the first rate of change to generate a first lag compensated first data.

6. The method of claim 5 wherein calibrating the first data further includes:
   determining a first calibration parameter associated with the first data based on the reference data point and the first lag compensated first data; and
   generating a calibrated first data based on the first calibration parameter and the first lag compensated first data.

7. The method of claim 5 wherein updating the calibrated first data includes:
   determining a second rate of change of the first data at the first predetermined time based on the second data; and
   performing a second lag compensation of the first data based on the second rate of change of the first data to generate a second lag compensated first data.

8. The method of claim 7 wherein calibrating the second data includes:
   determining a second calibration parameter associated with the first data based on the reference data point and the second lag compensated first data; and
   generating a calibrated second data based on the second calibration parameter and the second lag compensated first data.

9. A computer implemented method, comprising:
   determining a calibration parameter associated with a detected analyte value based from an analyte sensor in fluid contact with an interstitial fluid;
   calibrating the analyte value based on the calibration parameter to generate a calibrated analyte value using a processor; and
   dynamically updating the calibration parameter including updating the calibrated analyte value.

10. The method of claim 9 further including calibrating a second detected analyte value based on the dynamically updated calibration parameter.

11. The method of claim 9 wherein dynamically updating the calibration parameter includes:
   determining a rate of change of the detected analyte value; and
   generating a lag compensated analyte value based on the rate of change.

12. The method of claim 9 wherein calibrating the analyte value includes:
   determining a sensitivity associated with the detected analyte value; and
   applying the sensitivity to the lag compensated analyte value.

13. The method of claim 11 wherein dynamically updating the calibration parameter includes:
   updating the rate of change of the detected analyte value; and
   updating the lag compensated analyte value.

14. The method of claim 13 wherein updating the rate of change includes determining the rate of change of the detected analyte value between a first predetermined time and a second predetermined time.

15. The method of claim 11 wherein calibrating the analyte value includes:
   detecting a calibration data;
   determining a sensitivity based on the calibration data and the lag compensated analyte value; and
   generating a lag compensated and calibrated analyte value.

16. The method of claim 15 wherein the calibration data includes a blood glucose value.

17. An apparatus, comprising:
   one or more processing units; and
   a memory for storing instructions which, when executed by the one or more processors, causes the one or more processing units to obtain a reference data point at a first predetermined time, receive a first data from an analyte sensor at the first predetermined time, calibrate the first data based on the reference data point; receive a second data from an analyte sensor at a second predetermined time; update the calibrated first data based on the second data; and calibrate the second data.

18. The apparatus of claim 17 wherein the reference data point includes a blood glucose value.

19. The apparatus of claim 17 wherein the first predetermined time includes a calibration time associated with the calibration of one or more of the first data or the second data.

20. The apparatus of claim 17 wherein the first data and the second data includes a respective one of a monitored analyte value.

21. The apparatus of claim 17 wherein the memory is further configured for storing instructions which, when executed by the one or more processing units, causes the one or more processing units to determine a first rate of change of the first data at the first predetermined time, and to perform a first lag compensation of the first data based on the first rate of change to generate a first lag compensated first data.

22. The apparatus of claim 21 wherein the memory is further configured for storing instructions which, when executed by the one or more processing units, causes the one or more processing units to determine a first calibration parameter associated with the first data based on the reference data point and the first lag compensated first data and to generate a calibrated first data based on the first calibration parameter and the first lag compensated first data.

23. The apparatus of claim 21 wherein the memory is further configured for storing instructions which, when executed by the one or more processing units, causes the one or more processing units to determine a second rate of change of the first data at the first predetermined time based on the second data, and to perform a second lag compensation of the first data based on the second rate of change of the first data to generate a second lag compensated first data.

24. The apparatus of claim 23 wherein the memory is further configured for storing instructions which, when executed by the one or more processing units, causes the one or more processing units to determine a second calibration parameter associated with the first data based on the reference data point and the second lag compensated first data, and to generate a calibrated second data based on the second calibration parameter and the second lag compensated first data.

* * * * *

UNITED STATES PATENT AND TRADEMARK OFFICE
CERTIFICATE OF CORRECTION

PATENT NO. : 7,618,369 B2
APPLICATION NO. : 11/537991
DATED : November 17, 2009
INVENTOR(S) : Hayter et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 503 days.

Signed and Sealed this

Nineteenth Day of October, 2010

David J. Kappos
*Director of the United States Patent and Trademark Office*